(12) United States Patent
Krzysik et al.

(10) Patent No.: US 6,475,197 B1
(45) Date of Patent: Nov. 5, 2002

(54) ABSORBENT ARTICLES HAVING SKIN HEALTH BENEFITS

(75) Inventors: Duane Gerard Krzysik, Appleton, WI (US); David Roland Otts, Appleton, WI (US); Beth Anne Lange, Appleton, WI (US); Brenda Marie Nelson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/382,018

(22) Filed: Aug. 24, 1999

(51) Int. Cl.[7] .................. A61F 13/00; A61F 13/15; A01N 25/34
(52) U.S. Cl. .................. 604/304; 604/358; 424/402; 424/443; 514/865; 514/847
(58) Field of Search ................ 604/304, 358, 604/391; 424/401, 402, 443; 514/865, 847

(56) References Cited

U.S. PATENT DOCUMENTS

| | | |
|---|---|---|
| 3,896,807 A | 7/1975 | Buchalter |
| 4,100,324 A | 7/1978 | Anderson et al. |
| 4,273,786 A | 6/1981 | Kraskin |
| 4,381,782 A | 5/1983 | Mazurak et al. |
| 4,478,853 A | 10/1984 | Chaussee |
| 4,559,157 A | 12/1985 | Smith et al. |
| 4,604,281 A | 8/1986 | Deckner et al. |
| 4,604,313 A | 8/1986 | McFarland et al. |
| 4,690,821 A | 9/1987 | Smith et al. |
| 4,704,116 A | 11/1987 | Enloe |
| 4,798,603 A | 1/1989 | Meyer et al. |
| 4,818,464 A | 4/1989 | Lau |
| 4,842,593 A | 6/1989 | Jordan et al. |
| 4,846,823 A | 7/1989 | Enloe |
| 4,904,524 A | 2/1990 | Yoh |
| 5,019,073 A | 5/1991 | Roessler et al. |

(List continued on next page.)

FOREIGN PATENT DOCUMENTS

| | | |
|---|---|---|
| GB | 880276 A | 10/1961 |
| WO | WO 9731620 A2 | 9/1997 |
| WO | WO 9913861 A1 | 3/1999 |
| WO | WO 9937744 A2 | 7/1999 |
| WO | WO 99/45973 | 9/1999 |
| WO | WO 99/45974 | 9/1999 |
| WO | WO 99/45976 | 9/1999 |
| WO | WO 00/64407 A1 | 11/2000 |
| WO | WO 00/64408 A1 | 11/2000 |
| WO | WO 00/64409 | 11/2000 |

OTHER PUBLICATIONS

Fluhr, J.W. et al., "Glycerol Accelerates Recovery of Barrier Function In Vivo," Acta Derm Venereol, 1999; 79: pp. 418–421.

(List continued on next page.)

Primary Examiner—Kim M. Lewis
(74) Attorney, Agent, or Firm—Patricia A. Charlier

(57) ABSTRACT

A superior skin barrier enhancing body facing material on an absorbent article, can be made applying, on the outer surface of the body facing material, a melted lipid-enriched hydrophilic composition comprising a hydrophilic solvent, a high molecular weight polyethylene glycol, a fatty alcohol ($C_{14}$–$C_{30}$ or greater), humectant, an oil-in-water emulsifying surfactant having an HLB range greater than 7, a sterol or sterol derivative, and a natural fat or oil, and thereafter resolidifying the composition to form a distribution of solid compositon on the outer surface of the body facing material.

43 Claims, 2 Drawing Sheets

U.S. PATENT DOCUMENTS

| | | |
|---|---|---|
| 5,079,003 A | 1/1992 | Scaffidi |
| 5,160,739 A | 11/1992 | Kanga |
| 5,176,671 A | 1/1993 | Roessler et al. |
| 5,192,606 A | 3/1993 | Proxmire et al. |
| 5,288,546 A | 2/1994 | Roessler et al. |
| 5,304,162 A | 4/1994 | Kuen |
| 5,318,555 A | 6/1994 | Siebers et al. |
| 5,350,624 A | 9/1994 | Georger et al. |
| 5,364,382 A | 11/1994 | Latimer et al. |
| 5,374,262 A | 12/1994 | Keuhn, Jr. et al. |
| 5,386,595 A | 2/1995 | Kuen et al. |
| 5,399,219 A | 3/1995 | Roessler et al. |
| 5,403,302 A | 4/1995 | Roessler et al. |
| 5,405,342 A | 4/1995 | Roessler et al. |
| 5,413,570 A | 5/1995 | Enloe |
| 5,415,644 A | 5/1995 | Enloe |
| 5,423,789 A | 6/1995 | Kuen |
| 5,429,629 A | 7/1995 | Latimer et al. |
| 5,486,166 A | 1/1996 | Bishop et al. |
| 5,490,846 A | 2/1996 | Ellis et al. |
| 5,508,034 A | 4/1996 | Bernstein |
| 5,509,915 A | 4/1996 | Hanson et al. |
| 5,599,338 A | 2/1997 | Enloe |
| 5,607,980 A | 3/1997 | McAtee et al. |
| 5,643,588 A | 7/1997 | Roe et al. |
| 5,643,899 A | 7/1997 | Elias et al. |
| 5,648,083 A | 7/1997 | Blieszner et al. |
| 5,651,862 A | 7/1997 | Anderson et al. |
| 5,653,970 A | 8/1997 | Vermeer |
| 5,656,278 A | 8/1997 | Enjolras |
| 5,674,511 A | 10/1997 | Kacher et al. |
| 5,738,859 A | 4/1998 | Posner |
| 5,744,145 A | 4/1998 | Bertoli et al. |
| 5,759,558 A | 6/1998 | Epstein et al. |
| 5,800,818 A | 9/1998 | Prugnaud et al. |
| 5,849,315 A | 12/1998 | Rerek et al. |
| 5,863,663 A | 1/1999 | Mackey et al. |
| 5,869,070 A | 2/1999 | Dixon et al. |
| 5,968,025 A | 10/1999 | Roe et al. |
| 6,086,858 A | 7/2000 | McEleney et al. |
| 6,118,041 A | 9/2000 | Roe et al. |
| 6,152,906 A | 11/2000 | Faulks et al. |
| 6,153,208 A | 11/2000 | McAtee et al. |
| 6,287,286 B1 | 9/2001 | Akin et al. |
| 6,287,581 B1 | 9/2001 | Krzysik et al. |
| 6,338,855 B1 | 1/2002 | Albacarys et al. |

OTHER PUBLICATIONS

Yang, L. et al., "Topical Stratum Corneum Lipids Accelerate Barrier Repair After Tape Stripping, Solvent Treatment and Some But Not All Types of Detergent Treatment," British Journal of Dermatology, vol. 133, No. 5, Nov. 1995, pp. 679–685.

Derwent World Patent Database abstract of DE 4136540: Description of D. Pegaz, "Disposable Diaper".

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: E 96–92, "Standard Test Methods for Water Vapor Transmission of Materials," pp. 702–709, published Mar. 1992.

Feingold, Kenneth R., MD, "Permeability Barrier Homeostasis: Its Biochemical Basis and Regulation," *Cosmetics & Toiletries*, vol. 112, Jul. 1997, pp. 49, 50, 53–59.

Ghadially, Ruby, MD, et al., "Effects of petrolatum on stratum corneum structure and function," *Journal of the American Academy of Dermatology*, vol. 26, No. 3, Mar. 1992, pp. 387–396.

Wilkinson, J.B. et al., Editors, "Skin Creams," *Harry's Cosmeticology*, Seventh Edition, Chemical Publishing, New York, 1982, pp. 54–67.

ABSORBENT ARTICLES HAVING SKIN HEALTH BENEFITS

FIELD OF THE INVENTION

The present invention relates to the incorporation of a lipid-enriched hydrophilic lotion on the body facing material of disposable absorbent articles, such as diapers, training pants, adult incontinence products, under pants, and feminine care products, and the like. More particularly, the present invention relates to improving skin health via enhancement of skin barrier function by the delivery of lipids and humectants of a hydrophilic lotion from the body facing material of absorbent articles to the skin.

BACKGROUND OF THE INVENTION

The stratum corneum is the outer-most layer of the skin and is responsible for regulating skin water levels and functioning as a barrier against chemicals and other stressors found in the environment. The complex arrangement of lipids in the intercellular space of the stratum corneum is responsible for the establishment of normal barrier function. Multi-layered structures of cholesterol, ceramides, and fatty acids, as well as some other minor lipids, provides the major barrier to the transport of hydrophillic substances into the or through the skin. The link between the barrier function and skin health is apparent from the skin inflammation caused by lipid extraction from the skin.

Skin barrier can be damaged due to a number of mechanisms. Physical abrasion, for example caused by the repeated rubbing of abrasive materials, such as absorbent tissues or wipes, on the skin, strips away layers of the skin and thus damages skin barrier. Biological fluids, such as urine, feces and vaginal secretions, may contain a variety of components that can damage skin barrier. Examples of these components include proteases, lipases, and bile acids. Once the skin barrier is compromised, these components, in addition to other constituents of biological fluids, can initiate or exacerbate skin inflammation.

Diaper dermatitis, for example, is a genre of skin conditions that, in large part, originate from impaired barrier function. Impairment of the skin barrier can result from a variety of factors, including; increased skin hydration due to the occlusion of the skin caused by diapers, enzymatic skin damage due to fecal and urinary enzymes, and from physical damage imparted by wiping with a wet wipe.

Excessive hydration also has a negative impact on skin barrier. The hydration level of diapered skin, for example, may reach between five to ten times that of undiapered skin. Frequent contact of diapered skin with urine may also contribute to increased skin hydration. Increased skin hydration disrupts skin lipid organization in the stratum corneum. This disruption may increase-the skin permeability of irritants from feces and urine, thus increasing the risk of skin inflammation.

Diapered skin is normally cleansed several times a day with wipes utilizing solutions containing surfactants. The surfactants can extract lipids from the stratum corneum or disorganize the lipid structure within the stratum corneum, thereby decreasing the barrier function. The wipe material can cause physical damage to the skin and thus lead to decreased barrier function.

Typically, barrier creams, lotions and ointments are used to provide an artifical hydrophobic barrier on the skin. These products typically contain mineral oils, petrolatum and silicones that are heavy, greasy to the touch, and are typically used to treat, rather than prevent skin irritation.

Disposable absorbent articles such as diapers, training pants, adult incontinence products, absorbent under pants, and feminine care products have been used to absorb body fluids and leave the skin dry. Disposable absorbent articles of this type generally comprise a liquid impermeable back sheet member, an absorbent core or assembly, and a liquid permeable bodyside liner. It is the bodyside liner or other body facing material that comes into contact with the wearer's skin. While the body facing material is made of a soft compliant material, it can abrade the skin during use and may not leave the skin completely dry and free of the bodily fluids, such as solid or semi-solid waste, the absorbent article is trying to absorb. During frequent insults of bodily fluids and frequent use of disposable absorbent articles, the skin can become so abraded as to appear red and be sore to the touch.

To reduce skin irritation and abrasion, additive formulations can be applied to the body facing material such that, in use, the additive formulation either provides lubricity thereby reducing abrasive contact, or leaves the body facing material and is deposited on the skin where it can soothe the skin.

Once deposited on the skin, these additive formulations provide a skin benefit by occluding the skin surface due to the hydrophobic waxes present in the formulation. Thus, these formulations provide a short-term benefit by providing an artificial barrier, even though the underlying stratum corneum is still damaged.

To date, these additive formulations have been liquids or oil based and typically from petroleum (lipophilic materials) based semi-solids or oil based solids at room temperature. The liquid or oil based semi-solid type of formulations require a high amount of formulation added to the body facing material to deliver the benefit of reduced skin irritation and redness because these formulations absorb into a body facing material, leaving less on the surface to provide the benefit.

The oil based solid formulations can be applied heated (slightly above the melting point of the formulation) to the surface of a body facing material thereafter resolidifying the formulation on the surface(s) of the body facing material where the formulation is readily available for transfer to the users skin to protect the skin from or prevent further irritation and redness in an efficient cost-effective manner. However, since these formulations are lipophilic, it is sometimes difficult to incorporate hydrophilic or water soluble surfactants, cosmetic materials or active ingredients.

Thus, there is a need for a formulation that is basically hydrophilic that can be applied to a body facing material of a disposable absorbent article which will transfer sufficient formulation to protect, maintain, and recover skin barrier function and thus protect the skin from or prevent further irritation and redness in an efficient cost-effective manner.

SUMMARY OF THE INVENTION

It has now been discovered that a skin barrier enhancing disposable absorbent articles can be made applying, on the outer surface of the body facing material, a melted hydrophilic composition comprising a hydrophilic solvent, a high molecular weight polyethylene glycol, a fatty alcohol ($C_{14}$–$C_{30}$ or greater), a humectant, an oil-in-water emulsifying surfactant having an HLB range greater than 7, a sterol or sterol derivative, and a natural fat or oil, and thereafter resolidifying the composition to form a distribution of a melted lipid-enriched hydrophilic composition on the outer surface of the body facing material. Because the hydrophilic composition is a solid at room temperature and rapidly solidifies after application, it has less tendency to penetrate and migrate into the body facing material. Compared to body facing material treated with liquid formulations, this leaves a greater percentage of the added solid lotion composition on the surface of the body facing material where it can contact and transfer to the user's skin to provide a benefit. Furthermore, a lower add-on amount can be used to deliver the same benefit at a lower cost because of the efficient placement of the composition substantially at the surface of the body facing material of the absorbent articles.

Hence, in one aspect, the present invention is a hydrophilic composition comprising from about 10 to about 90 weight percent hydrophilic solvent, from about 5 to about 95 weight percent high molecular weight polyethylene glycol (preferably having a molecular weight of about 720 or greater), from about 1 to about 30 weight percent of a $C_{14}$ to $C_{30}$ or greater fatty alcohol, from about 0.5 to about 30 weight percent of humectant, from about 1 to about 20 weight percent emulsifying surfactant having an HLB range greater than 7, from about 0.1 to about 10 weight percent of sterol or sterol derivative, and from about 0.1 to about 30 weight percent of natural fats or oils. The hydrophilic composition may have a melting point from about 30° C. to about 100° C. and a process viscosity of greater than 50 centipoise. The composition may also have a penetration hardness of from about 5 millimeters to 360 millimeters.

In another aspect, the present invention is a body facing material wherein the outer surface of the body facing material have solidified deposits of a hydrophilic composition comprising from about 10 to about 90 weight percent hydrophilic solvent, from about 5 to about 95 weight percent high molecular weight (defined as a solid at room temperature) polyethylene glycol (preferably having a molecular weight of about 720 or greater), from about 1 to about 30 weight percent of a $C_{14}$ to $C_{30}$ or greater fatty alcohol, from about 0.5 to about 30 weight percent of humectant, from about 1 to about 20 weight percent emulsifying surfactant having an HLB range greater than 7, from about 0.1 to about 10 weight percent of sterol or sterol derivative, and from about 0.1 to about 30 weight percent of natural fats or oils. The hydrophilic composition may have a melting/freezing point of from about 30° C. to about 100° C. and a process viscosity of greater than 50 centipoise. The composition may also have a penetration hardness from about 5 millimeters of penetration to 360 millimeters of penetration.

In another aspect, the present invention is a method of making a body facing material in an absorbent article comprising: (a) heating a composition comprising a hydrophilic solvent, high molecular weight polyethylene glycol, a fatty alcohol, a humectant, an emulsifying surfactant having an HLB range greater than 7, a sterol or sterol derivative, and a natural fat or oil to a temperature above the melting point of the composition, causing the composition to melt; (b) uniformly applying the melted composition to the outer surface of the body facing material web in spaced-apart deposits; and (c) resolidifying the deposits of the melted composition. The hydrophilic composition may have a melting point of from about 30° C. to about 100° C.

DETAILED DESCRIPTION OF THE INVENTION

Figure 1:
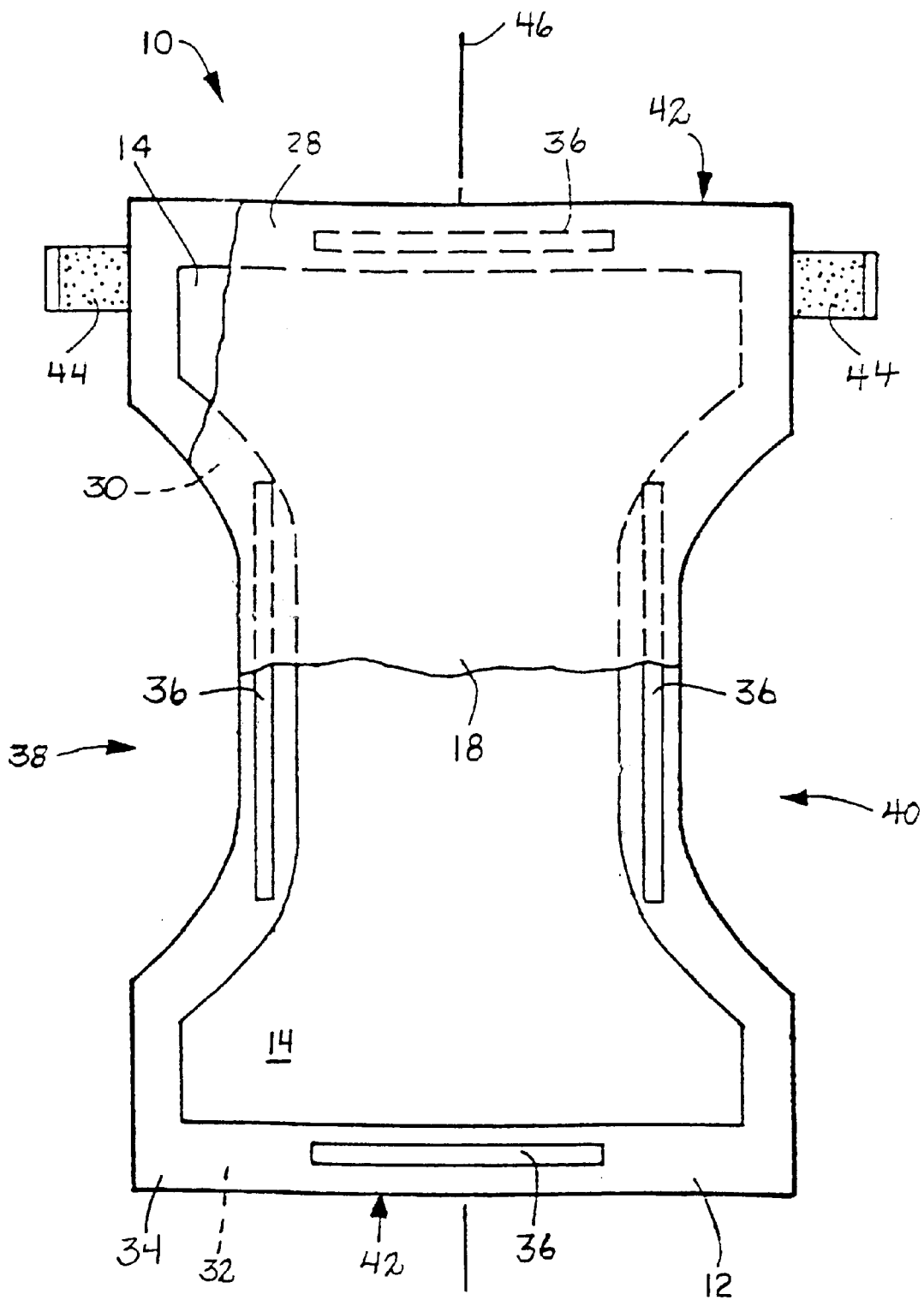
FIG. 1 representatively shows a partially cutaway, top plan view of an absorbent article according to one embodiment of the present invention.

One embodiment of the present invention is a body facing material having an outer surface with solidified deposits of a lipid-enriched hydrophilic composition. The composition may comprise from about 10 to about 90 weight percent hydrophilic solvent, from about 5 to about 95 weight percent high molecular weight polyethylene glycol having a molecular weight of about 720 or greater, from about 1 to about 30 weight percent of a $C_{14}$ to $C_{30}$ or greater fatty alcohol, from about 0.5 to about 10 weight percent of humectant, from about 1 to about 20 weight percent of oil-in-water emulsifying surfactant having an HLB range greater than 7, from about 0.1 to about 10 weight percent of sterol or sterol derivative, and from about 0.1 to about 30 weight percent of natural fats or oils.

The composition may have a melting point from about 30° C. to about 100° C. The composition may have a process viscosity of greater than about 50 centipoise. The composition may have a penetration hardness of from about 5 millimeters to about 360 millimeters. The add-on amount of the composition may be from about 0.1 grams per meter squared ($g/m^2$) to about 30 $g/m^2$ of the material, and more preferably from about 0.5 $g/m^2$ to about 25 $g/m^2$.

The hydrophilic solvent used in the composition may include water, propylene glycol, a low molecular weight polyethylene glycol, glycerin, or hydrogenated starch hydrolysate. The fatty alcohol used in the composition may include cetyl alcohol, stearyl alcohol, arachidyl alcohol, or behenyl alcohol. The molecular weight of the high molecular weight polyethylene glycol used in the composition may be from about 720 to about 1,840,000 daltons, and more specifically from about 1,400 to about 440,000 daltons. The high molecular weight polyethylene glycol used in the composition may include polyethylene glycol 1,400 daltons, polyethylene glycol 8,000 daltons, or polyethylene glycol 10,000 daltons. The humectant used in the composition may include glycerin, sorbitol, or hydrogenated starch hydrolysate. The surfactant used in the composition may include glyceryl stearate SE, glycol stearate SE, or sorbitan stearate. The sterol or sterol derivative used in the composition may include soy sterol, cholesterol, or lanasterol. The natural fat or oil used in the composition may include sunflower oil, borage oil, or avocado oil.

Another embodiment of the present invention is a method of making a soft body facing material having an outer surface comprising: (a) heating a composition comprising a hydrophilic solvent, a high molecular weight polyethylene glycol, a fatty alcohol, a humectant, an oil-in-water emulsifying surfactant having an HLB range greater than 7, a natural fat or oil, and a sterol or sterol derivative, to a temperature above the melting point of the composition, causing the composition to melt; (b) applying said melted composition to said outer surface of a body facing material web in spaced-apart deposits; and (c) resolidifying the deposits of the melted composition.

The composition may have a melting point of from about 30° C. to about 100° C. The composition may have a process viscosity of greater than about 50 centipoise. The resolidified composition may have a penetration hardness of from about 5 to about 360 millimeters. The melted composition may be applied by spraying. The melted composition may be applied by spraying, slot coating, or printing.

Another embodiment of the present invention is composition that enhances skin barrier comprising from about 5 to about 90 weight percent hydrophilic solvent, from about 5 to about 95 weight percent high molecular weight polyethylene glycol having a molecular weight of about 720 or greater, from about 1 to about 25 weight percent of a $C_{14}$ to $C_{30}$ or greater fatty alcohol, from about 0.5 to about 10 weight percent of humectant, from about 1 to about 20 weight percent of oil-in-water emulsifying surfactant having an HLB range greater than 7, and from about 0.1 to about 10 weight percent of sterol or sterol derivative.

The composition may have a melting point from about 30° C. to about 100° C. The composition may have a process viscosity of greater than about 50 centipoise. The resolidified composition may have a penetration hardness of from about 5 to about 360 millimeters.

The hydrophilic solvent of the composition may be selected from the group consisting of: water, propylene glycol, low molecular weight polyethylene glycol, glycerin, sorbitol, hydrogenated starch hydrolysate, silicone glycol, and mixtures thereof. The fatty alcohol of the composition may be selected from the group consisting of: cetyl alcohol, stearyl alcohol, arachidyl alcohol, behenyl alcohol, and mixtures thereof.

The high molecular weight polyethylene glycol of the composition may be selected from the group consisting of: polyethylene glycols having a average molecular weight greater than 720 daltons. The humectant of the composition may be selected from the group consisting of: glycerin, propylene glycol, sorbitol, polyethylene glycol, hydrogenated starch hydrolysates, sodium PCA, potassium PCA, sodium lactate, and mixtures thereof. The surfactant of the composition may be selected from the group consisting of: glyceryl stearate SE, glyceryl stearate, glycol stearate SE, glycol stearate, and mixtures thereof.

The sterol or sterol derivative of the composition may be selected from the group consisting of: cholesterol, sitosterol, stigmasterol, and ergosterol, lanasterol, soy sterol, avocado sterols, cholesterol esters, sterol esters, and mixtures thereof. The natural fat or oil of the composition may be selected from the group consisting of: avocado oil, apricot oil, babassu oil, borage oil, camellia oil, canola oil, castor oil, coconut oil, corn oil, cottonseed oil, evening primrose oil, hydrogenated cottonseed oil, hydrogenated palm kernal oil, maleated soybean oil, meadowfoam oil, palm kernal oil, phospholipids, rapeseed oil, palmitic acid, stearic acid, linoleic acid, rose hip oil, sunflower oil, soybean oil, derivatives of natural fats or oils (such as stearyl alcohol, lauryl alcohol, myristyl alcohol, benenyl alcohol, and the like), and the like, and mixtures thereof.

The amount of the hydrophilic solvent used in the composition may be from about 5 to about 90 weight percent, and more specifically from about 25 to about 75 percent. The amount of the high molecular weight polyethylene glycol used in the composition may be from about 5 to about 95 weight percent, and more specifically from about 15 to about 50 weight percent.

The amount of the fatty alcohol used in the composition may be from about 1 to about 30 percent. The amount of the surfactant used in the composition may be from about 1 to about 20 percent. The amount of the sterol or sterol derivative used in the composition may be from about 0.1 to about 10 percent. The amount of said natural fat or oil used in the composition may be from about 0.1 to about 30 percent.

One embodiment of the composition comprises about 48.2 weight percent propylene glycol, about 20 weight percent polyethylene glycol 8000, about 20 weight percent stearyl alcohol about 5 weight percent glycerin, about 3 weight percent glyceryl stearate SE, about 0.8 weight percent soy sterol, and about 3 weight percent borage oil.

Another embodiment of the composition comprises about 34 weight percent propylene glycol, about 20 weight percent polyethylene glycol 8000, about 10 weight percent stearyl alcohol, about 10 weight percent behenyl alcohol, about 15 weight percent glycerin, about 5 weight percent propylene glycol oleate SE, about 1 weight percent cholesterol, and about 5 weight percent sunflower oil.

Another embodiment of the composition comprises about 42.2 weight percent propylene glycol, about 20 weight percent polyethylene glycol 8000, about 20 weight percent stearyl alcohol, about 5 weight percent glycerin, about 2 weight percent glyceryl stearate SE, about 0.8 weight percent soy sterol, and about 10 weight percent borage oil.

Another embodiment of the composition comprises about 42.2 weight percent propylene glycol, about 20 weight percent polyethylene glycol 8000, about 20 weight percent stearyl alcohol, about 5 weight percent glycerin, about 2 weight percent glyceryl stearate SE, about 0.8 weight percent soy sterol, and about 10 weight percent avocado oil.

Another embodiment of the composition comprises about 42.2 weight percent propylene glycol, about 20 weight percent polyethylene glycol 8000, about 20 weight percent stearyl alcohol, about 5 weight percent glycerin, about 2 weight percent glyceryl stearate SE, about 0.8 weight percent soy sterol, and about 10 weight percent lanolin oil.

Another embodiment of the composition comprises about 42.2 weight percent propylene glycol, about 20 weight percent polyethylene glycol 10,000, about 20 weight percent behenyl alcohol, about 5 weight percent glycerin, about 2 weight percent glyceryl stearate SE, about 0.8 weight percent avocadin, and about 10 weight percent sunflower oil.

Another embodiment of the composition comprises about 32.2 weight percent polyethylene 200, about 20 weight percent polyethylene glycol 1,000, about 30 weight percent behenyl alcohol, about 5 weight percent hydrogenated starch hydrolysate, about 2 weight percent glyceryl stearate SE, about 0.8 weight percent avocadin, and about 10 weight percent sunflower oil.

Another embodiment of the composition comprises about 32.2 weight percent polyethylene 200 about 20 weight percent polyethylene glycol 1,000, about 30 weight percent behenyl alcohol, about 5 weight percent hydrogenated starch hydrolysate, about 2 weight percent glyceryl stearate SE, about 0.8 weight percent avocadin, and about 10 weight percent sunflower oil.

Another embodiment of the composition comprises about 37 weight percent polyethylene 200, about 20 weight percent polyethylene glycol 8,000, about 10 weight percent behenyl alcohol, about 10 weight percent stearyl alcohol, about 5 weight percent hydrogenated starch hydrolysate, about 5 weight percent glycol stearate SE, about 3 weight percent avocado sterols, and about 10 weight percent borage oil.

Another embodiment of the composition comprises about 20 weight percent polyethylene glycol 200, about 20 weight percent propylene glycol, about 20 weight percent polyethylene glycol 8,000, about 10 weight percent behenyl alcohol, about 10 weight percent stearyl alcohol, about 5 weight percent sodium PCA, about 5 weight percent glycol stearate SE, about 2 weight percent cholesterol, and about 8 weight percent borage oil.

Another embodiment of the composition comprises about 42 weight percent polyethylene 200, about 20 weight percent polyethylene glycol 8,000, about 10 weight percent behenyl alcohol, about 10 weight percent stearyl alcohol, about 5 weight percent glycerin, about 5 weight percent glycol stearate SE, about 3 weight percent soy sterol, and about 5 weight percent evening primrose oil.

Another embodiment of the present invention is a method for enhancing/restoring/maintaining the skin barrier function of a user. The method comprises the steps of:

a) contacting a body facing material on the skin of the user wherein said material comprises a skin barrier enhancing/restoring/maintaining composition that provides a skin barrier enhancing/restoring/maintaining benefit upon transfer of the composition to said user's skin;

b) transferring at least a portion of the composition during use of the body facing material; and, c) repeating steps a) and b) with one or more additional body facing material with sufficient frequency to enhance/restore/maintain said skin barrier in an area of skin contacted by the body facing material, relative to skin contacted by an equivalent body facing material that does not comprise the skin barrier enhancing/restoring/maintaining composition.

The skin barrier enhancing/restoring/maintaining composition of the method comprises from about 5 to about 90 weight percent hydrophilic solvent, from about 5 to about 95 weight percent high molecular weight polyethylene glycol having a molecular weight of about 720 or greater, from about 1 to about 25 weight percent of a $C_{14}$ to $C_{30}$ or greater fatty alcohol, from about 0.5 to about 10 weight percent of humectant, from about 1 to about 20 weight percent of oil-in-water emulsifying surfactant having an HLB range greater than 7, and from about 0.1 to about 10 weight percent of sterol or sterol derivative.

The composition may have a melting point from about 30° C. to about 100° C. The resolidified composition may have a process viscosity greater than about 50 centipoise. The resolidified composition may have a penetration hardness of from about 5 to about 360 millimeters. The method may further comprise using a body facing material having a skin-barrier enhancing/restoring/maintaining composition by the user on each use occasion. The method may further comprise using a body facing material which does not comprise a skin-barrier enhancing/restoring/maintaining composition by the user intermittently. The method may further comprise using the body facing material comprising a skin-barrier enhancing/restoring/maintaining composition by a user whose skin is compromised and with sufficient frequency to improve skin-barrier function.

The amount of hydrophilic solvent, including water if present, in the hydrophilic composition can be from about 10 to about 90 weight percent, more specifically from about 25 to about 75 weight percent, more specifically from about 30 to about 60 weight percent. As used herein, suitable hydrophilic solvents include, but are not limited to, the following materials: water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol solutions, hydrogenated starch hydrolysate, and silicone glycols, and the like, as well as mixtures thereof.

The amount of high molecular weight polyethylene glycol in the hydrophilic composition can be from about 5 to about 95 weight percent, more specifically from about 10 to about 50 weight percent, and still more specifically from about 15 to about 25 weight percent. The high molecular weight polyethylene glycol in the hydrophilic lotion compositions of the present invention primarily functions as an immobilizing agent for the hydrophilic solvent and any active ingredient. In addition to immobilizing the solvent, and reducing its tendency to migrate, the high molecular weight polyethylene glycol in the hydrophilic lotion composition provides a tackiness to the hydrophilic lotion composition which improves the transfer to the skin of the wearer. As used herein, suitable high molecular weight polyethylene glycols include, but are not limited to, the following materials: polyethylene glycols having an average molecular weight of 720 or greater, and the like, as well as mixtures thereof. These materials are not liquid at room temperature. Particularly suitable high molecular weight polyethylene glycols can have an average molecular weight of from 720 to about 1,840,000, more specifically from about 1400 to about 440,000, and still more specifically from about 1760 to about 10,570.

The amount of fatty alcohol in the hydrophilic composition can be from about 1 to about 30 weight percent, more specifically from about 10 to about 25 weight percent, and still more specifically from about 15 to about 20 weight percent. As used herein, suitable fatty alcohols include, but not limited to, the following materials: alcohols having a carbon chain length of $C_{14}$–$C_{30}$ or greater, including cetyl alcohol, stearyl alcohol, arachidyl alcohol, and behenyl alcohol, and the like as well as mixtures thereof.

The amount of humectant in the hydrophilic composition can be from about 0.5 to about 30 weight percent, more specifically from about 1 to about 20 weight percent, and still more specifically from about 5 to about 10 weight percent. Humectants are typically cosmetic ingredients used to increase the water content of the top layers of the skin. This groups of materials includes primarily hydroscopic ingredients. As used herein, suitable humectants include, but are not limited to, the following materials: Acetamide MEA, Aloe Vera Gel, Arginine PCA, Chitosan PCA, Copper PCA, Corn Glycerides, Dimethyl Imidazolidinone, Fructose, Glucamine, Glucose, Glucose Glutamate, Glucuronic Acid, Glutamic Acid, Glycereth-7, Glycereth-12, Glycereth-20, Glycereth-26, Glycerin, Honey, Hydrogenated Honey, Hydrogenated Starch Hydrolysate, Hydrolyzed Corn Starch, Lactamide MEA, Lactic Acid, Lactose Lysine PCA, Mannitol, Methyl Gluceth-10, Methyl Gluceth-20, PCA, PEG-2 Lactamide, PEG-10 Propylene Glycol, Polyamino Sugar Condensate, Potassium PCA, Propylene Glycol, Propylene Glycol Citrate, Saccharide Hydrolysate, Saccharide Isomerate, Sodium Aspartate, Socium Lactate, Sodium PCA, Sorbitol, TEA-Lactate, TEA-PCA, Urea, Xylitol, and the like, as well as mixtures thereof.

The amount of oil-in-water emulsifying surfactant having an HLB range greater than 7 in the hydrophilic composition can be from about 1 to about 20 weight percent, more specifically from about 2 to about 15 weight percent, and still more specifically from about 3 to about 10 weight percent. Emulsifying surfactants are employed typically in cosmetic preparations to form emulsions of various components. The immiscible phase, such as an oil, is dispersed as droplets in the continuous phase, such as water or in this case the hydrophilic solvent.

The preferred surfactants include, but not limited to Emulsifying Wax NF, Glyceryl Stearate, Glyceryl Stearate SE, Glycol Stearate, Glycol Stearate SE, Glycereth-20 Stearate, Glyceryl Behenate, Glyceryl Hydroxystearate, Glyceryl Laurate SE, Glyceryl Oleate, Glyceryl Oleate SE, Propylene Glycol Oleate, Propylene Glycol Oleate SE, Propylene Glycol Stearate, Propylene Glycol Stearate SE, Sorbitan Stearate, Sorbitan Trioleate, and the like, as well as mixtures thereof.

The amount of a sterol or sterol derivatives or mixture of sterols and sterol derivatives in the hydrophilic composition can be from about 0.1 to about 10 weight percent, more specifically from about 0.5 to about 5 weight percent, and still more specifically from about 0.8 to about 3 weight percent. As used herein, suitable sterols and sterol derivatives include, but are not limited to, the following materials: β-sterols having a tail on the 17 position and having no polar groups, for example cholesterol, sitosterol, estigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyidecanoate, ergocalciferol, tall oil sterol, soy sterol acetate, lanasterol, soy sterol, avocado sterols, cholesterol esters, sterol esters, and the like, as well as mixtures thereof.

The amount of a natural fat or oil or a mixture of natural fats or oils in the hydrophilic composition can be from about 0.1 to about 30 weight percent, more specifically from about 0.5 to about 20 weight percent, and still more specifically from about 1 to about 10 weight percent. As used herein, the phrase natural fats or oils is understood to include fats, oils, essential oils, fatty acids, fatty alcohols, phopholipids, and mixtures thereof. As used herein, suitable natural fats or oils include, but are not limited to, the following materials:

Fats and Oils: Apricot Kernel Oil, Avocado Oil, Babassu Oil, Borage Seed Oil, Butter, $C_{12}$–$C_{18}$ Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$–$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$–$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, and the like, as well as mixtures thereof.

Fatty Acids: Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Fatty Alcohols: Behenyl Alcohol, $C_9$–$C_{11}$ Alcohols, $C_{12}$–$C_{13}$ Alcohols, $C_{12}$–$C_{15}$ Alcohols, $C_{12}$–$C_{16}$ Alcohols, $C_{14}$–$C_{15}$ Alcohols, Caprylic Alcohol, Cetearyl Alcohol, Cetyl Alcohol, Coconut Alcohol, Decyl Alcohol, Hydrogenated Tallow Alcohol, Lauryl Alcohol, Myristyl Alcohol, Oleyl Alcohol, Palm Alcohol, Palm Kernel Alcohol, Stearyl Alcohol, Tallow Alcohol, Tridecyl Alcohol, and the like, as well as mixtures thereof.

Essential Oils: Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

In some embodiments of the present invention, the hydrophilic composition may contain petrolatum or mineral oil. The amount of petrolatum or mineral oil in the composition can be from about 0 to about 20 weight percent, more specifically from about 0 to about 10 weight percent, and still more specifically from about 0 to about 5 weight percent.

As used herein, the term 'body facing material' includes, but is not limited to, materials such as: body side liner; elastic material; tissue; intake and distribution material, absorbent material, including, but not limited to coform, woven and nonwoven materials, back sheet liner material, or any other material known in the art that are or can be used in the construction of personal care absorbent articles, such as diapers, training pants, absorbent underpants, adult incontinence product, feminine hygiene products. The term 'body facing material' is understood to include materials that are both typically and less frequently in contact with the wearer's skin. The body facing material of the present invention can be a single layer or multi-layers.

The composition of the present invention can be applied to a specific portion or component of the absorbent article or to the entire surface of the absorbent article that comes into contact with the wearer's skin during use of the absorbent article. In addition, the composition can be applied in varying concentration or deposition amounts on the skin contacting surface of the absorbent article or portion thereof. The compositions are applied such that the compositions will be delivered via contact with the user's skin during the use of the absorbent article. The compositions of the present invention can be applied after the body facing material has been incorporated into the absorbent article or prior to incorporating the body facing material into the absorbent article. The phrase 'effective amount of the composition' is understood to mean an amount of the composition of the present invention which, when applied to the body facing material, will be effective in providing skin barrier enhancing benefits.

Some additional examples of materials that may serve as body facing material in the present invention are discussed in the following patent applications: "Absorbent Article Having Improved Breathability", U.S. Ser. No. 09/139,820, filed on Aug. 25, 1998 with Michael J. Faulks and Pamela J. Mayberry as inventors; "Absorbent Article Having a High Air Exchange Rate", U.S. Ser. No. 09/139,824, filed on Aug. 25, 1998 with Michael J. Faulks, Pamela J. Mayberry, Sue C. Paul, Audra S. Wright, and Frank J. Akin as inventors; and, "Absorbent Article Having a Reduced Growth of *Candida Albican* S", U.S. Ser. No. 09/328,681, filed on Jun. 9, 1999 (claiming priority to a provisional application filed Aug. 25, 1998 with U.S. Serial No. 60/097,810 PROV) with Michael J. Faulks, Pamela J. Mayberry, Sue C. Paul, and Audra S. Wright as inventors, the entire disclosures of which are herein incorporated by reference to the extent it is consistent herewith.

Resolidification of the deposits of the hydrophilic composition can occur almost instantaneously, without the need for external cooling means such as chill rolls, if the composition is heated to a temperature only slightly above or at the melting point of the composition. However, external means such as chill rolls, either before or after the application of melt, can be used if desired to accelerate resolidification. Such instantaneous resolidification tends to impede penetration of the composition into the bodyside liner 18 or tissue material 20 and retain it on the outer surface 28 of the bodyside liner 18 or tissue material 20, which is advantageous. For example, the temperature of the melted composition can advantageously be above the melting point about 10° C. or less, more specifically about 5° C. or less and still more specifically about 2° C. or less. As the temperature of the melted composition approaches the melting point, the viscosity of the melted composition generally increases, which further enhances the tendency of the melted composition to be retained on the outer surface 28.

For purposes herein, "melting point" is the temperature at which the majority of the melting occurs, it being recognized that melting actually occurs over a range of temperatures. The melting point of the compositions of this invention can be from about 30° C. to about 100° C., more specifically from about 40° C. to about 70° C., and still more specifically from about 50° C. to about 60° C.

In addition, for purposes herein, "penetration hardness" is the needle penetration in millimeters according to ASTM D 1321, "Needle Penetration of Petroleum Waxes. Lower needle penetration hardness values correspond to harder materials. The penetration hardness of the compositions of this invention can be from about 5 to 360 millimeters, more specifically from about 5 to about 200 millimeters, more specifically from about 5 to about 150 millimeters, and still more specifically from about 5 to about 100 millimeters. (Formulations having a needle penetration hardness greater than 360 millimeters cannot be measured using ASTM method D 1321).

The hardness of the formulations or compositions of this invention is important for two reasons. First, the softer the formulation the more mobile the formulation will be, making the formulation more likely to migrate to the interior of the bodyside liner 18 or tissue material 20 as well as the absorbent core 14, which is not desirable. Secondly, softer formulations tend to be more greasy/oily to the touch, which is also less desirable. In general, formulations having a needle penetration hardness of from about 200 to 360 millimeters feel creamy to slightly greasy with less smoothness (depending on additives). Formulations that have needle penetration hardness values of from about 5 to about 200 millimeters feel silky to creamy and very smooth (depending on additives).

The melt point viscosity and/or the process temperature viscosity of the formulations or compositions of this invention is important for two reasons: First, the higher the melt point viscosity or the process temperature viscosity as it is applied to the outside surface of the diaper liner, the formulation is less likely to penetrate through to the inner surface of the diaper liner. The less formulation penetrate through the liner the more there is on the surface of the liner where it can readily transfer to the wearers skin surface. Secondly, the higher the viscosity of the formulation at the above or at the melting point of the formulation, the less likely the formulation will migrate at typical or adverse storage conditions.

In order to better enhance the benefits to consumers, additional ingredients can be used. The classes of ingredients and their corresponding benefits include, without limitation: antifoaming agents (reduce the tendency of foaming during processing); antimicrobial actives; antifungal actives; antiseptic actives; antioxidants (product integrity to prevent oxidation of the natural oils and other ingredients in the formulation); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product including vitamins); colorants (impart color to the product); deodorants (reduce or eliminate unpleasant odor and protect against the formation of malodor on body surfaces); emollients (help to maintain the soft, smooth, and pliable appearance of the skin by their ability to remain on the skin surface or in the stratum corneum to act as lubricants, to reduce flaking, and to improve the skin's appearance); film formers (to hold active ingredients on the skin by producing a continuous film on skin upon drying); fragrances (consumer appeal); natural moisturizing agents (NMF) and other skin moisturizing ingredients known in the art; opacifiers (reduce the clarity or transparent appearance of the product); skin conditioning agents; skin protectants (a drug product which protects injured or exposed skin or mucous membrane surface from harmful or annoying stimuli); solvents (liquids employed to dissolve components found useful in the cosmetics or drugs); UV absorbers; and, surfactants (as solubilizing agents, suspending agents and wetting agents).

In addition, to these classes of ingredients, from about 0.01 to about 20 weight percent of oil soluble/dispersible or lipophilic materials can be easily emulsified into the formulation using anionic, amphoteric, cationic, nonionic and/or zwitterionic surfactants. Lipophilic materials without limitation include: silicones/organomodified silicones (protection, tissue water resistance, lubricity, tissue softness); emollients, fatty esters and, the like. Powders to enhance lubricity, oil adsorption, provide skin protection, astringency, opacity, etc. and microencapsulated ingredients can also be dispersed into the formulation.

The minimum level of the composition to be applied to the bodyside liner 18 or tissue material 20 is an amount effective for reducing abrasion or irritation of the skin of the wearer. The total bodyside liner 18 or tissue material 20 add-on of the composition can be from about 0.5 to about 40 weight percent, more specifically from about 5 to about 30 weight percent, and more specifically from about 10 to about 15 weight percent, based on the weight of the bodyside liner 18 or tissue material 20. The add-on amount will depend upon the desired effect of the composition on the product attributes and the specific composition.

A preferred method to uniformly apply the heated composition to the outer surface 28 of the web of body facing material is spraying or slot coating. However, other printing methods, such as flexographic printing or rotogravure printing can be used.

As used herein, all recited ranges of amounts, temperatures, molecular weights and penetration hardnesses are intended to include all sub-ranges within the recited ranges, even though not specifically stated.

As used herein, the term "absorbent article" refers to articles or products that are used to absorb and contain bodily fluids. Disposable absorbent articles include such products as diapers, training pants, adult incontinence articles, absorbent under pants, and feminine care products that have been used to absorb body fluids and leave the skin dry.

Figure 2:
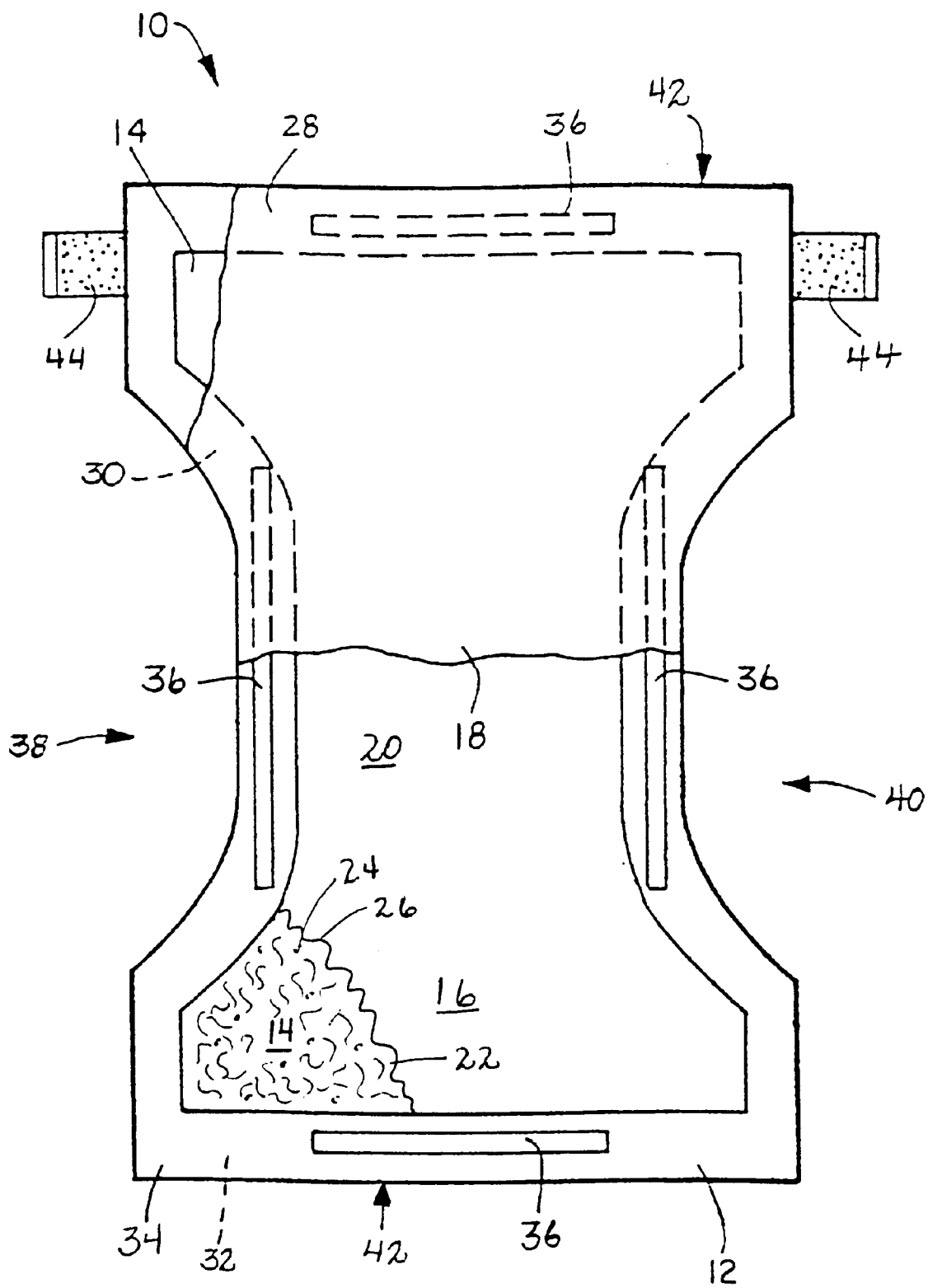
FIG. 2 representatively shows a partially cutaway, top plan view of an absorbent article according to another embodiment of the present invention.

Disposable absorbent articles 10 of this type generally comprise a liquid impermeable back sheet member 12, an absorbent core 14 or absorbent assembly 16, and a liquid permeable bodyside liner 18. (See FIGS. 1 and 2.) It is the bodyside liner 18 or tissue material 20 that comes into contact with the wearer's skin. Typically, the back sheet member 12 is joined to the bodyside liner 18 with the absorbent core 14 disposed between the back sheet member 12 and the bodyside liner 18. A general description of these components, the back sheet member 12, the bodyside liner 18, and the absorbent core 14, will be discussed below.

In general, the absorbent core 14 absorbs and retains bodily fluids, such as urine, menses, and other body exudates. The absorbent core 14 is preferably compressible, conformable, and non-irritating to the wearer's skin. The absorbent core 14 may take a variety of sizes and shapes, such as rectangular, oval, hourglass, "T" shaped, asymmetric, dog bone, and the like. The absorbent core 14 may be comprised of a wide variety of liquid absorbent materials commonly used in absorbent articles 10. Absorbent cores 14 typically include a porous fibrous matrix of fluff fibers 22 and high absorbency material 24.

The porous fibrous matrix of fluff fibers 22 of absorbent core 14 is preferably an air laid batt of fluff and high absorbency material 24 which may be formed in many ways, for example according to the teaching of Mazurak and Fries as set forth in U.S. Pat. No. 4,381,782 the entire disclosure of which is incorporated herein by reference. The absorbent core 14 can comprise an air-formed mixture of high absorbency material 24 (SAP) and fluff fibers 22, preferably of fluff pulp. The mixing of the fluff fibers 22 and the high absorbency material 24 can be homogeneous, graduated, or layered. Also, the fluff fibers 22, other than fluff pulp such as chemically stiffened and thermo-mechanical pulps, can be used.

In addition, the absorbent core 14 can comprise absorbent material other than air formed fluff fibers 22 and SAP 24. For example, coform materials as referenced in U.S. Pat. No. 4,818,464 to Lau and U.S. Pat. No. 4,100,324 to Anderson can be used to make the absorbent as long as they also contain high absorbency materials. In addition, wet formed composite materials comprising a combination of fibers and high absorbency materials as disclosed in U.S. Pat. No. 5,651,862 to Anderson et al. can also be used. Stabilized air-laid materials comprising a mixture of fibers, binder fibers, and high absorbency materials which are bound together by latex binding or through air bonding are also usable as absorbent materials. Additionally, any material known in the art that serves to absorb body exudates can be used to construct the absorbent core 14 as shown in the present invention.

The high absorbency materials 24 are typically hydrogel polymers that are desirably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company (Drytech 2035 LD), Hoechst-Celanese Corporation and Allied-Colloid. Typically, the high-absorbency material 24 is capable of absorbing at least about 15 times its weight in water, and desirably is capable of absorbing more than about 25 times its weight in water.

The high-absorbency material 24 can be distributed or otherwise incorporated into the absorbent core 14 employing various techniques. For example, the high-absorbency material 24 can be substantially uniformly distributed among the fluff fibers 22 comprising the absorbent core 14. The materials can also be non-uniformly distributed within the fluff fibers 22 of the absorbent core 14 to form a generally continuous gradient with either an increasing or decreasing concentration of the high-absorbency material 24, as determined by observing the concentration moving inward from the back sheet member 12. Alternatively, the high-absorbency material 24 can comprise a discrete layer separate from the fluff fibers 22 of the absorbent core 14, or can comprise a discrete layer integral. with the absorbent core 14.

The absorbent core 14 may also include a wrap layer 26 to help maintain the integrity of the fibrous absorbent core 14. (See FIG. 2.) This wrap layer 26 may comprise a cellulosic tissue or spunbond, meltblown or bonded-carded web material composed of synthetic polymer filaments, such as polypropylene, polyethylene, polyesters or the like or natural polymer filaments such as rayon or cotton. The wrap layer 26 may be made of the same materials as those used in the bodyside liner 18 or be made of materials differing from those used in the bodyside liner 18. In some cases, the bodyside liner 18 may be absent, and the wrap layer 26, also referred to as the tissue material 20, will serve as the bodyside layer of the absorbent article 10, coming in contact with the wearer's skin.

The absorbent core 14 can include additional components to assist in the acquisition, distribution, and storage of bodily exudates, such as a dusting layer, a transport layer, a wicking or acquisition/distribution layer, an intake layer, or a surge layer. See U.S. Pat. No. 4,798,603 issued Jan. 17, 1989, to Meyer et al., or a surge management layer, such as described in U.S. Pat. No. 5,486,166 issued Jan. 23, 1996, to Bishop et al., U.S. Pat. No. 5,364,382 issued Nov. 15, 1994, to Latimer et al., U.S. Pat. No. 5,490,846 to Ellis et al., U.S. Pat. No. 5,429,629 to Latimer et al., U.S. Pat. No. 5,509,915 to Hanson et al., U.S. Pat. No. 5,192,606 to Proxmire et al.

The bodyside liner 18 consists of a nonwoven or other soft material for contacting the wearer's skin. The bodyside liner 18 has an outer (exterior) surface 28 that faces toward the wearer and an inner (interior) surface 30 that faces away from the wearer. The bodyside liner 18 is described in more detail below. The bodyside liner 18 is compliant and soft feeling to the wearer. The bodyside liner 18 may be any soft, flexible, porous sheet that is aqueous liquid permeable, permitting aqueous liquids to readily penetrate into its thickness. A suitable bodyside liner 18 may be manufactured from a wide range of materials, such as natural fibers (e.g., wood or cotton fibers), synthetic fibers (e.g., polyester or polypropylene fibers) or from a combination of natural and synthetic fibers or reticulated foams and apertured plastic films.

The bodyside liner 18 is formed of an aqueous liquid permeable material so that aqueous liquid waste, and possibly semi-solid waste as well, can pass through to the absorbent core 14 and be absorbed by the absorbent core 14 of the absorbent article 10. A suitable bodyside liner 18 may be comprised of a nonwoven web, a spunbond, meltblown or bonded-carded web composed of synthetic polymer filaments or fibers, such as polypropylene, polyethylene, polyesters or the like, a perforated film, or a web or natural polymer filaments or fibers such as rayon or cotton.

In addition, the bodyside liner 18 may be treated with a surfactant to aid in aqueous liquid transfer. Suitably, the bodyside liner 18 is a nonwoven spunbond. Suitably, the spunbond material is available from Kimberly-Clark Corporation, located in Roswell, Ga. The bodyside liner 18 has a weight from about 0.3 oz. per square yard (osy) to about 2.0 osy and alternatively about 0.5 osy. The bodyside liner 18 of the underpant maybe printed, colored or decoratively embossed. The bodyside liner 18 can also be a nonwoven web or sheet of polyolefin fibers, such as polypropylene, polyester, polyethylene, Rayon, chisso and the like. The bodyside liner 18 may also be a plastic film with perforations, an expanded plastic webbing material or a scrim material. The bodyside liner 18 has a pore size that readily allows the passage therethrough of air, sweat, perspiration due to the breathability of the material. The bodyside liner 18 may be selectively embossed or perforated with discrete slits or holes extending therethrough.

Ideally, the fabric of the bodyside liner 18 is surface treated with a surfactant such as that commercially available from Union Carbide Chemicals and Plastics Company, Inc., of Danbury, Conn., U.S.A. under the trade designation TRITON X-102. As used herein, the term "fabric" refers to all of the woven, knitted and nonwoven fibrous webs. The term "nonwoven web" means a web of material that is formed without the aid of a textile weaving or knitting process.

As an alternate material, an aqueous liquid permeable bodyside liner 18 can be made of a carded web of polyester fibers bonded to a spunbonded polypropylene or polyethylene carrier sheet. The carded material is made up of about 20 to about 60 weight percent polypropylene or polyethylene and about 80 to about 40 weight percent polyester. The basis weight of this material can be between about 30 gsm and about 70 gsm.

Also, as used herein, a "liner", "liner product", "diaper liner", "top sheet", "tissue" can be a bodyside liner 18 or the tissue material 20 of a personal care absorbent article 10, such as diapers, training pants, absorbent underpants, adult incontinence products feminine hygiene products, or the like. The bodyside liner 18 or the tissue material 20 of this invention can be a single layer or multi-layers. In all cases, the compositions are typically applied to the outer surface 28 of the bodyside liner 18 or the tissue material 20 of the disposable absorbent article 10. The compositions of the present invention can be applied after the bodyside liner 18 or tissue material 20 has been incorporated into the absorbent article 10 or prior to incorporating the bodyside liner 18 or the tissue material 20 into the absorbent article 10.

The back sheet member 12 is needed to prevent aqueous liquid strike through to the outer clothing when bodily fluid is discharged onto the absorbent core 14 of the absorbent article 10. The back sheet member 12 typically consists of an aqueous liquid impermeable film such as polyethylene. The aqueous liquid impermeable back sheet member 12 has an outer (exterior) surface 32 that faces away from the wearer and an inner (interior) surface 34 that faces toward the wearer. In construction of the disposable absorbent article 10, the back sheet member 12, acting as a barrier, should retard the movement of the aqueous liquid through the absorbent article 10 by making the back sheet member 12 resistant to penetration normally encountered under wearing conditions. The back sheet member 12 desirably comprises a material that is formed or treated to be aqueous liquid impermeable.

Alternatively, the back sheet member 12 may comprise an aqueous liquid permeable material and other suitable means (not shown), such as an aqueous liquid impermeable layer associated with the absorbent core 14 may be provided to impede aqueous liquid movement away from the absorbent core 14 of the absorbent article 10. The disposable absorbent article 10 may be rendered aqueous liquid impermeable by any method well known in the art such as coating the absorbent core 14 or by securing a separate aqueous liquid impermeable material to the absorbent core 14. The back sheet member 12 may comprise a thin, aqueous liquid impermeable web or sheet of plastic film such as polyethylene, polypropylene, polyvinyl chloride or similar material. Other acceptable materials include a single spunbonded layer of the above types of materials, two layers of spunbonded and meltblown materials or a three-layer material of spunbonded-meltblown-spunbonded material. Suitable foam materials may also be used, as well as materials that are both aqueous liquid impermeable and vapor-permeable.

Alternately, the back sheet member 12 may comprise a nonwoven, fibrous web which has been suitably constructed and arranged to have low aqueous liquid permeability. Still alternately, the back sheet member 12 may comprise a layered or laminated material, such as a thermally bonded plastic film and nonwoven web composite. Alternatively, the back sheet member 12 consists of a aqueous liquid impermeable film or foam which is permeable to water vapor under normal wearing conditions. More preferred, the back sheet member 12 has a water vapor transmission rate of at least about 800 grams/m$^2$/24 hours measured by ASTM E96-92. One example of a suitable film is a 39.4 grams per square meter microporous film produced by Mitsui and sold by Consolidated Thermoplastics (CT) under the tradename of ESPOIR® N-TAF-CT.

The absorbent articles 10 may also include elastic members 36 in the waist 42 (in absorbent articles 10 such as under pants and briefs), in the regions surrounding the leg openings 38 and 40, in the waist portions (not shown) as fit elastics (in absorbent articles 10 such as under pants), in side panels (not shown) (in absorbent articles 10 such as briefs and under pants), and in flap or barrier structures(not shown). The elastic members 36 may be in the form of strips, ribbons, connected ribbons or strips, sheets, strands, bands, threads, filaments, or any combination of these shapes and others known to the art. The elastic members 36 may also be of latent elastic material that is activated after placement in the absorbent articles 10.

The compositions of the present invention are solid or semisolid at 30° C. As used herein, the term "semisolid" refers to a composition having a rheology typical of pseudoplastic or plastic fluids. Because the compositions are in at as least a semisolid state at ambient temperatures, migration of the composition is minimized. The compositions, being solid or semisolid at ambient temperatures, do not have the tendency to migrate into the interior of the bodyside liner 18 or the tissue material 20 and ultimately into the absorbent article 10 to which the composition has been applied. The compositions are transferable to the wearer's skin by normal contact, movement of the wearer, or the body heat of the wearer.

The composition is applied to the outer surface 28 of the bodyside liner 18 or the tissue material 20 of the absorbent article 10. Any of a variety of application methods that evenly distribute lubricious materials having a molten or liquid consistency can be used. Suitable methods include spraying, slot coating, printing (such as flexographic printing), coating (such as gravure coating), extrusion, or combinations of these methods, such as spraying the composition on a rotating surface, then transferring the composition to the outer surface 28 of the bodyside liner 18 or the tissue material 20.

The manner of applying the composition to the bodyside liner 18 or the tissue material 20 should be such that the bodyside liner 18 or the tissue material 20 does not become saturated with the composition. If the bodyside liner 18 or the tissue material 20 becomes saturated with the composition, the fluid permeability of the bodyside liner 18 or the tissue material 20 may be reduced or blocked. In addition, saturation of the bodyside liner 18 or the tissue material 20 is not necessary to obtain therapeutic or protective benefits from the composition of the present invention.

A variety of fastening means 44 can be used for securing the absorbent article 10 around or in contact with the wearer including tape fasteners, belts, ties, disposable and reusable garments, and mechanical type fasteners. The mechanical type fasteners include buttons, button holes, snaps, buckles, clasps, hooks and loops, end extensions, tabs, and the like which are designed or adapted to interlock or engage some type of a complimentary device or the outer cover of the absorbent article 10. Suitable engaging elements for such mechanical closure elements include self-engaging geometric shaped materials, such as hooks, loops, snaps, buckles, bulbs, mushrooms, arrowheads, balls on stems, male and female mating components, or the like. In addition, elasticized fasteners are also used in assuring better fit of such absorbent articles 10. Examples of some fastening systems and securement members are disclosed in U.S. Pat. No. 5,423,789 to Kuen; U.S. Pat. No. 5,405,342 to Roessler et al.; U.S. Pat. No. 5,403,302 to Roessler et al.; U.S. Pat. No. 5,399,219 to Roessler et al.; U.S. Pat. No. 5,386,595 to Kuen et al.; U.S. Pat. No. 5,374,262 to Kuen, Jr. et al.; U.S. Pat. No. 5,318,555 to Siebers et al.; U.S. Pat. No. 5,304,162 to Kuen; U.S. Pat. No. 5,288,546 to Roessler et al.; U.S. Pat. No. 5,176,671 to Roessler et al.; U.S. Pat. No. 5,176,671 to Roessler et al.; and, U.S. Pat. No. 5,019,073 to Roessler et al.

The disposable absorbent articles 10 may also include flap or gasket structures (not shown). These flap or gasket structures can be assembled in a number of different configurations, including those disclosed in U.S. Pat. No. 4,704,116 issued to Enloe on Nov. 3, 1987, U.S. Pat. No. 4,846,823 issued to Enloe on Jul. 11, 1989, U.S. Pat. No. 5,413,570 issued to Enloe on May 9, 1995, U.S. Pat. No. 5,415,644 issued to Enloe on May 16, 1995 and U.S. Pat. No. 5,599,338 issued to Enloe on Feb. 4, 1997.

The compositions of the present invention may be applied to the entire outer surface 28 of the bodyside liner 18 or tissue material 20 or portions thereof. Preferably, the composition is applied in a stripe or pattern aligned with a centered on the longitudinal centerline 46 of the disposable absorbent article 10. (See FIG. 1.) The dimensions of the stripe or pattern will vary with the different absorbent articles 10 to which the composition is being applied.

The compositions of the present invention may be applied non-uniformly to the outer surface 28 of the bodyside liner 18 or tissue material 20. The term "non-uniformly", as used herein, refers to the amount, pattern of distribution, thickness of the application, or the like, of the composition can be varied over the outer surface 28 of the bodyside liner 18 or tissue material 20. The composition could be applied to the inner surface 30 of the bodyside liner 18 or tissue material 20, alone or in combination with the application of the composition to the outer surface 28.

The compositions of the present invention can be applied to the bodyside liner 18 or tissue material 20 at any point during assembly of the absorbent article 10. For example, the raw material web being formed into the bodyside liner 18 or tissue material 20 may be treated with the composition before the web is processed into the bodyside liner 18 or tissue material 20; the bodyside liner 18 or tissue material 20 may be treated with the composition before being incorporated into the absorbent article 10; and, the bodyside liner 18 or tissue material 20 may be treated with the composition after the bodyside liner 18 or tissue material 20 has been incorporated into the absorbent article 10.

EXAMPLES

The following examples are presented to provide a more detailed understanding of the invention. The particular materials and parameters are exemplary and are not intended to limit the scope of the invention.

The following formulas are used in Examples 1–2:

|  | weight percent |
|---|---|
| Formula 1 | |
| Water | qs to 100% |
| Glycerin | 5% |
| Glyceryl stearate SE | 3% |
| Borage oil | 1% |
| Aloe | 0.3% |
| Tocopherol acetate | 0.3% |
| Suitable pH adjuster to pH 5.5 | |
| Formula 2 | |
| Water | qs to 100% |
| Glycerin | 5% |
| Glyceryl stearate SE | 3% |
| Borage oil | 1% |
| Soy sterol | 0.8% |
| Aloe | 0.3% |
| Tocopherol acetate | 0.3% |
| Suitable pH adjuster to pH 5.5 | |
| Formula 3 | |
| Water | qs to 100% |
| Glycerin | 5% |

-continued

| | weight percent |
|---|---|
| Glyceryl stearate SE | 3% |
| Borage oil | 1% |
| Soy sterol | 0.8% |
| Prolipid 141 (International Specialty Products, Wayne, NJ) | 1% |
| Aloe | 0.3% |
| Tocopherol acetate | 0.3% |
| Suitable pH adjuster to pH 5.5 | |

(PROLIPID is commercially available from International Specialty Products located in Wayne, N.J. PROLIPID is generally described in U.S. Pat. No. 5,849,315 to Rerek et al. which issued Dec. 15, 1998; which is herein incorporated by reference to the extent it is consistent herewith.)

| | weight percent |
|---|---|
| Formula 4 | |
| Water | qs to 100% |
| Lipomicron NSLE, (Sederma, Le Perray-en-Yvelines, France) | 5% |
| Formula 5 | |
| Water | qs to 100% |
| Glycerin | 5% |
| Sterol Esters | 0.5% |
| Petrolatum | 1% |
| Avocadin | 0.5% |
| ProLipid 141 (International Specialty Products, Wayne, NJ) | 1% |

Example 1

Lipid-enriched formulations for treatment of absorbent articles Promote barrier repair as measured by Transepidermal water loss (TEWL).

All studies were conducted in a temperature and humidity controlled room (71° F.±5° F.; 40%±5% relative humidity).

1A. Twenty microliters of a lipid-enriched formula for treatment of an absorbent article was topically applied to the volar forearm of 24 female panelists following abrasion with emery cloth. TEWL measurements were obtained using a Dermalab evaporimeter pre- and post abrasion and 1,2, and 4 hours after application of the formulas. Mean TEWL values are expressed in Table 1.1. Repeated measures ANOVA was used to adjust for the repeated TEWL measures.

Table 1.1: TEWL (g/m²/hr) Results—Lipid-enriched Absorbent Article Formulations

| | Post Abrasion Mean | 1 Hour Mean | 2 Hour Mean | 4 Hour Mean |
|---|---|---|---|---|
| Formula 1 | 17.0 | 9.7* | 9.9* | 10.3 |
| Formula 2 | 15.5 | 8.7* | 8.4* | 8.2* |
| Formula 3 | 18.4 | 9.7* | 8.6* | 8.6* |
| Untreated | 17.4 | 12.7 | 12.0 | 11.5 |

*denotes significantly different than untreated site.

All lipid-enriched absorbent article formulations repaired the skin barrier compared to the untreated site at 1,2 and 4 hours after application of the formulas as measured by TEWL.

1B. Mean TEWL values following the same study design described above are expressed in Table 1.2. The pre-abrasion (baseline) TEWL values were subtracted from all of the other readings so as to correct for underlying subject-to-subject differences. All statistical evaluations were made on these differences.

TABLE 1.2

TEWL (g/m²/hr) Results- Lipid-enriched absorbent article formulations

| | Post Abrasion Mean | 1 Hour Mean | 2 Hour Mean | 4 Hour Mean |
|---|---|---|---|---|
| Formula 4 | 12.0 | 6.4* | 5.6* | 5.1* |
| Formula 5 | 12.3 | 2.7*,** | 2.4*,** | 2.7*,** |
| Untreated | 11.5 | 9.9 | 9.6 | 10.0 |

*denotes significantly different than untreated site
**denotes significantly different than formula 5

Both formula 4 and 5 repaired the skin barrier compared to the untreated site as measured by TEWL. In addition, Formula 5 repaired the barrier significantly better than Formula 4. Formula 4 contains Lipomicron NSLE, a Sederma (Le Perray-en-Yvelines, France) product at the recommended use level that is marketed as a product for protection of the cutaneous barrier.

Example 2

Lipid-enriched absorbent article formulations enhance skin moisturization as measured by conductance.

All studies were conducted in a temperature and humidity controlled room (71° F.±5° F.; 40±5% relative humidity).

2A. Twenty microliters of a lipid-enriched formula for treatment of an absorbent article was topically applied to the volar forearm. Conductance measurements were obtained using the Skicon instrument before application of the formulas and 1,2, 4, and 6 hours post application. Mean conductance values are expressed in Table 2.1. A pair-wise comparison for each time period using univariate ANOVAs was appplied.

TABLE 2.1

Conductance- Lipid-enriched absorbent article formulations

| | Baseline Mean | 1 Hour Mean | 2 Hour Mean | 4 Hour Mean | 6 Hour Mean |
|---|---|---|---|---|---|
| Formula 1 | 197.7 | 366.5* | 365.7* | 349.7* | 345.4* |
| Formula 2 | 182.8 | 298.6* | 297.5* | 311.5* | 304.6* |
| Formula 3 | 168.2 | 299.1* | 302.8* | 296.5* | 296.4* |
| Untreated | 164.3 | 178.3 | 176.9 | 175.0 | 176.3 |

*denotes significantly different than untreated site.

All lipid-enriched absorbent article formulas significantly enhanced skin moisturization at 1, 2, 4 and 6 hours post application of the formulas compared to the untreated site.

2B. Mean Conductance values following the same study design described above with the exception that a conductance measure was not obtained at 6 hours post application are expressed in Table 2.2. The pre-application (baseline) conductance values were subtracted from all of the other readings so as to correct for underlying subject-to-subject differences. All statistical evaluations were made on these differences.

TABLE 2.2

Conductance - Lipid-enriched absorbent article formulations

|  | 1 Hour Mean | 2 Hour Mean | 4 Hour Mean |
| --- | --- | --- | --- |
| Formula 4 | 50.7 | 40.3 | 39.1 |
| Formula 5 | 194.0* | 166.6* | 142.2* |
| Untreated | 31.7 | 17.3 | 12.3 |

*denotes significantly different than untreated site.

Formula 5 significantly enhanced skin moisturization at 1, 2 and 4 hours post application of the formulas compared to the untreated site. Formula 4 failed to enhance skin moisturization at any of the times tested. Formula 4 contains Lipomicron NSLE, a Sederma (Le Perray-en-Yvelines, France) product at the recommended use level that is marketed as a product for protection of the cutaneous barrier.

It can be appreciated that the above example formulations can be easily incorporated into the compositions described within this invention and deliver equivalent skin health benefits.

Thus, the Examples representatively illustrate that the lipid-enriched hydrophilic composition of the present invention may provide absorbent article products having improved softness as well as providing improved protection of the skin barrier function. Accordingly, the different aspects of the present invention can advantageously provide absorbent article products which, when compared to conventional absorbent article products, are softer and have improved protection of skin barrier function. Such absorbent article products can advantageously be used for as diapers, training pants, adult incontinence products, under pants, and feminine care products, and the like.

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

We claim:

1. A body facing material having an outer surface, wherein said outer surface of said body facing material has a composition that enhances skin barrier consisting of:
   from about 10 to about 90 weight percent hydrophilic solvent;
   from about 5 to about 95 weight percent high molecular weight polyethylene glycol having a molecular weight of about 720 or greater;
   from about 1 to about 30 weight percent of a $C_{14}$ to $C_{30}$ or greater fatty alcohol;
   from about 0.5 to about 10 weight percent of humectant;
   from about 1 to about 20 weight percent of oil-in-water emulsifying surfactant having an HLB range greater than 7;
   from about 0.1 to about 10 weight percent of sterol or sterol derivative; and,
   from about 0.1 to about 30 weight percent of natural fats or oils.

2. The material of claim 1, wherein said composition has a melting point from about 30° C. to about 100° C.

3. The material of claim 1, wherein said composition has a process viscosity of greater than about 50 centipoise.

4. The material of claim 1, wherein said composition has a penetration hardness of from about 5 millimeters to about 360 millimeters.

5. The material of claim 1, wherein the add-on amount of said composition is from about 0.1 grams per meter squared ($g/m^2$) to about 30 $g/m^2$ on said material.

6. The material of claim 1, wherein the add-on amount of said composition is from about 0.1 grams per meter squared ($g/m^2$) to about 30 $g/m^2$ of said material.

7. The material of claim 1, wherein said hydrophilic solvent is water.

8. The material of claim 1, wherein said hydrophilic solvent is propylene glycol.

9. The material of claim 1, wherein said hydrophilic solvent is a low molecular weight polyethylene glycol.

10. The material of claim 1, wherein said hydrophilic solvent is glycerin.

11. The material of claim 1, wherein said hydrophilic solvent is hydrogenated starch hydrolysate.

12. The material of claim 1, wherein said fatty alcohol is cetyl alcohol.

13. The material of claim 1, wherein said fatty alcohol is stearyl alcohol.

14. The material of claim 1, wherein said fatty alcohol is arachidyl alcohol.

15. The material of claim 1, wherein said fatty alcohol is behenyl alcohol.

16. The material of claim 1, wherein said molecular weight of said high molecular weight polyethylene glycol is from about 720 to about 1,840,000 daltons.

17. The material of claim 1, wherein said molecular weight of said high molecular weight polyethylene glycol is from about 1,400 to about 440,000 daltons.

18. The material of claim 1, wherein said high molecular weight polyethylene glycol is polyethylene glycol 1,400.

19. The material of claim 1, wherein said high molecular weight polyethylene glycol is polyethylene glycol 8,000.

20. The material of claim 1, wherein said high molecular weight polyethylene glycol is polyethylene glycol 10,000.

21. The material of claim 1, wherein said humectant is glycerin.

22. The material of claim 1, wherein said humectant is sorbitol.

23. The material of claim 1, wherein said humectant is hydrogenated starch hydrolysate.

24. The material of claim 1, wherein said surfactant is glyceryl stearate SE.

25. The material of claim 1, wherein said surfactant is glycol stearate SE.

26. The material of claim 1, wherein said surfactant is sorbitan stearate.

27. The material of claim 1, wherein said sterol or sterol derivative is soy sterol.

28. The material of claim 1, wherein said sterol or sterol derivative is cholesterol.

29. The material of claim 1, wherein said sterol or sterol derivative is lanasterol.

30. The material of claim 1, wherein said natural fat or oil is sunflower oil.

31. The material of claim 1, wherein said natural fat or oil is borage oil.

32. The material of claim 1, wherein said natural fat or oil is avocado oil.

33. A method of making a body facing material that enhances skin barrier having an outer surface consisting: (a) heating a composition consisting a hydrophilic solvent, a high molecular weight polyethylene glycol, a fatty alcohol, a humectant, an oil-in-water emulsifying surfactant having an HLB range greater than 7, a natural fat or oil, and a sterol or sterol derivative, to a temperature above the melting point of said composition, causing said composition to melt, said composition having a melting point of from about 30° C. to about 100° C.; (b) applying said melted composition to said outer surface of a body facing material web; and (c) resolidifying said melted composition.

34. The method of claim 33, wherein said resolidified composition has a process viscosity of greater than about 50 centipoise.

35. The method of claim 33, wherein said resolidified composition has a penetration hardness of from about 5 to about 360 millimeters.

36. The method of claim 33, wherein said melted composition is applied by spraying.

37. A method for enhancing/restoring/maintaining skin barrier function skin of a user, comprising the steps of:
 a) contacting a body facing material on said skin of said user wherein said material comprises a skin barrier enhancing/restoring/maintaining composition that provides a skin barrier enhancing/restoring/maintaining benefit upon transfer of said composition to said user's skin;
 b) transferring at least a portion of said composition during use of said body facing material; and,
 c) repeating steps a) and b) with one or more additional body facing material with sufficient frequency to enhance/restore/maintain said skin barrier in an area of skin contacted by said body facing material, relative to skin contacted by an equivalent body facing material that does not comprise said skin barrier enhancing/ restoring/maintaining composition,
wherein said skin barrier enhancing/restoring/maintaining composition comprising: from about 5 to about 90 weight percent hydrophilic solvent, from about 5 to about 95 weight percent high molecular weight polyethylene glycol having a molecular weight of about 720 or greater, from about 1 to about 25 weight percent of a $C_{14}$ to $C_{30}$ or greater fatty alcohol, from about 0.5 to about 10 weight percent of humectant, from about 1 to about 20 weight percent of oil-in-water emulsifying surfactant having an HLB range greater than 7, and from about 0.1 to about 10 weight percent of sterol or sterol derivative.

38. The method of claim 37, wherein said composition having a melting point from about 30° C. to about 100° C.

39. The method of claim 37, wherein said resolidified composition has a process viscosity greater than about 50 centipoise.

40. The method of claim 37, wherein said resolidified composition has a penetration hardness of from about 5 to about 360 millimeters.

41. The method of claim 37, wherein said body facing material comprising said skin-barrier enhancing/restoring/ maintaining composition are used by said user on each use occasion.

42. The method of claim 37, wherein said body facing material which do not comprise a skin-barrier enhancing/ restoring/maintaining composition are used by said user intermittently.

43. The method of claim 37, wherein said body facing material comprising said skin-barrier enhancing/restoring/ maintaining composition are used by a user whose skin is compromised and are used with sufficient frequency to improve skin-barrier function.

* * * * *